(12) United States Patent
Sakyu et al.

(10) Patent No.: US 8,513,473 B2
(45) Date of Patent: Aug. 20, 2013

(54) METHOD FOR PRODUCING TRANS-1,3,3,3-TETRAFLUOROPROPENE

(75) Inventors: Fuyuhiko Sakyu, Iruma-gun (JP); Satoru Okamoto, Fujimino (JP); Yasuo Hibino, Shiki (JP)

(73) Assignee: Central Glass Company, Limited, Ube-shi (JP)

( * ) Notice: Subject to any disclaimer, the term of this patent is extended or adjusted under 35 U.S.C. 154(b) by 348 days.

(21) Appl. No.: 12/682,521

(22) PCT Filed: Oct. 7, 2008

(86) PCT No.: PCT/JP2008/068196
§ 371 (c)(1),
(2), (4) Date: Apr. 9, 2010

(87) PCT Pub. No.: WO2009/048048
PCT Pub. Date: Apr. 16, 2009

(65) Prior Publication Data
US 2010/0256426 A1    Oct. 7, 2010

(30) Foreign Application Priority Data
Oct. 10, 2007    (JP) .................................. 2007-263912

(51) Int. Cl.
*C07C 21/18*    (2006.01)
(52) U.S. Cl.
USPC ........................................................ 570/151
(58) Field of Classification Search
None
See application file for complete search history.

(56) References Cited

U.S. PATENT DOCUMENTS

| | | | |
|---|---|---|---|
| 7,485,760 B2 | 2/2009 | Wang et al. | |
| 7,563,936 B2 | 7/2009 | Wang et al. | |
| 7,638,660 B2 | 12/2009 | Wang et al. | |
| 2008/0051610 A1* | 2/2008 | Wang et al. | 570/156 |

FOREIGN PATENT DOCUMENTS

| | | |
|---|---|---|
| JP | 10-7605 A | 1/1998 |
| JP | 11-140002 A | 5/1999 |
| JP | 2008-69147 A | 3/2008 |
| JP | 2008-110979 A | 5/2008 |

OTHER PUBLICATIONS

I. L. Knunyants, et al., Communication 13. Catalytic Hydrogenation of Perfluoro Olefins, Institute of Heteroorganic Compounds, Aug. 1960, Academy of Sciences of the USSR, No. 8, pp. 1312-1317.
Fluorine Chemistry Synthesis, Journal of Fluorine Chemistry, 44 (1989) 167-174.
Dario Sianesi e Renso Fontanelli.—Fluoroolefine—Nota I. Cis e trans 1,2,3,3,3,-pentafluoropropilene., Apr. 26, 1965, Milano Linate.—Soc. Montecatini, Institu Unificato per le Ricerche di base 850-861.
International Search Report dated Sep. 9, 2008 with English Translation (Four (4) pages).
PCT/ISA/237 dated Dec. 9, 2008 (Four (4) pages).

* cited by examiner

*Primary Examiner* — Sudhakar Katakam
(74) *Attorney, Agent, or Firm* — Crowell & Moring LLP

(57) ABSTRACT

There is provided a method for producing trans-1,3,3,3-tetrafluoropropene, which includes the step of bringing cis-1,3,3,3-tetrafluoropropene into contact, in a gas phase, with a metal oxide, an activated carbon supporting thereon a metal compound, or a fluorinated derivative thereof, as a catalyst.

11 Claims, No Drawings

METHOD FOR PRODUCING TRANS-1,3,3,3-TETRAFLUOROPROPENE

TECHNICAL FIELD

The present invention relates to a method for producing trans-1,3,3,3-tetrafluoropropene (In the following description, 1,3,3,3-tetrafluoropropene is occasionally referred to as "OHFC-1234ze"). The present invention more particularly relates to a method for producing trans-1,3,3,3-tetrafluoropropene by isomerization of cis-1,3,3,3-tetrafluoropropene. It is herein noted that trans-1,3,3,3-tetrafluoropropene is useful as blowing agents for rigid polyurethane foams, solvents, detergents, refrigerants, hydraulic fluids, propellants, raw materials for fluoropolymers etc.

BACKGROUND ART

There are previously known production methods of 1,3,3,3-tetrafluoropropene, one of which involves a dehydrofluorination reaction of 1,1,1,3,3-pentafluropropane with potassium hydroxide in dibutyl ether (Non-Patent Document 1); another of which involves a fluorination reaction of 1-chloro-3,3,3-trifluoropropene with hydrogen fluoride in the presence of a Ti/C or Cr/C catalyst (Patent Document 1); and still another of which involves a dehydrofluorination reaction of 1,1,1,3,3-pentafluropropane in a gas phase by contact with a carbon or a metal-supported carbon in an elevated-temperature reaction range (Patent Document 2).

In each of these methods, however, the 1,3,3,3-tetrafluoropropene is obtained as a mixture of cis and trans isomers. This raises an inconvenience in the case of using either the cis or trans isomer of the 1,3,3,3-tetrafluoropropene.

Then, it has been tested to convert 1,2,3,3,3-pentafluoropropene, which is one kind of trifluoromethyl propene, from trans-1,2,3,3,3-pentafluoropropene to cis-1,2,3,3,3-pentafluoropropene (Non Patent Documents 2 and 3). More specifically, Non-Patent Document 2 reports a technique of isomerization of 1,2,3,3,3-pentafluoropropene by contact with antimony pentafluoride under pressurized conditions. Non-Patent Document 3 reports a technique of isomerization of 1,2,3,3,3-pentafluoropropene by heating at 350 to 550° C. or by ultraviolet radiation.

There is further a production method of trans-1,3,3,3-tetrafluoropropene by isomerization, which was laid open after the filing date of the earlier basic application of the present application (Patent Document 3). This method utilizes a fluorinated $Cr_2O_3$ catalyst as a fluorinated oxide catalyst and shows a conversion rate of 91.0% at a reaction temperature of 100° C. but a conversion rate of merely 5.8% at a reaction temperature of 30° C.

Non-Patent Document 1: Izvest. Akad. Nauk S. S. S. R., Otdel. Khim. Nauk., P.1412, 1960
Non Patent Document 2: J. Fluorine Chem., Vol. 44, 167, 1989
Non Patent Document 3: Ann. Chim. (Italy), Vol. 55, P. 850, 1965
Patent Document 1: Japanese Laid-Open Patent Publication No. 10-7605
Patent Document 2: Japanese Laid-Open Patent Publication No. 11-140002
Patent Document 3: Japanese Laid-Open Patent Publication No. 2008-110979

DISCLOSURE OF THE INVENTION

It is an object of the present invention to provide a method for producing trans-1,3,3,3-tetrafluoropropene industrially advantageously and efficiently by isomerization of cis-1,3,3,3-tetrafluoropropene.

In consideration of the conventional 1,2,3,3,3-pentafluoropeopene isomerization techniques mentioned in Background Art, there are problems that: it is difficult to handle the antimony pentafluoride as the antimony pentafluoride has very high hygroscopicity and reacts quickly with moisture in the air to form hydrogen fluoride (Non-Patent Document 2); and it is necessary to provide special equipment such as an ultraviolet radiation device or high-temperature heating device (Non Patent Document 3). Thus, it is hardly said that these isomerization techniques are suitable for industrial applications.

As a result of extensive researches, the present inventors have found that cis-1,3,3,3-tetrafluoropropene of the formula [1] can be isomerized to trans-1,3,3,3-tetrafluoropropene of the formula [2] by contact of the cis-1,3,3,3-tetrafluoropropene with a catalyst. The present inventors have further found that this isomerization reaction can be carried out in a much lower temperature range by the use of a specific kind of catalyst than by the use of the other catalyst and thus be advantageously used for industrial applications.

[Chem 1]

(1)

(2)

Namely, the present invention provides a method (designated as "first method") for producing trans-1,3,3,3-tetrafluoropropene by contact of cis-1,3,3,3-tetrafluoropropene with a catalyst, wherein the catalyst comprises a metal oxide that contains one kind or two or more kinds of metals, including 50 atomic % or more of aluminum in terms of metal atoms.

The first method may be characterized as a production method (designated as "second method") in which the metal oxide contains two or more kinds of metals, including at least one selected from the group consisting of chromium, titanium, manganese, iron, nickel, cobalt, magnesium, zirconium and antimony.

The first or second method may be characterized as a production method (designated as "third method") in which the metal oxide is a fluorinated metal oxide that has a part or all of oxygen atoms substituted with fluorine atoms.

The third method may be characterized as a production method (designated as "fourth method") in which the fluorinated metal oxide is fluorinated alumina.

The present invention further provides a method (designated as "fifth method") for producing trans-1,3,3,3-tetrafluoropropene by contact of cis-1,3,3,3-tetrafluoropropene with a catalyst, wherein the catalyst is a supported catalyst that comprises a compound of at least one kind of metal selected from the group consisting of aluminum, chromium, titanium, manganese, iron, nickel, cobalt, magnesium, zirconium and antimony, supported on a carbon.

Any one of the first to fifth methods may be characterized as a production method (designated as "sixth method") in which the cis-1,3,3,3-tetrafluoropropene is brought into contact, in a gas phase, with the metal oxide.

Any one of the first to sixth methods may be characterized as a production method (designated as "seventh method") in which the cis-1,3,3,3-tetrafluoropropene is brought into contact with the metal oxide at −10 to 400° C.

Any one of the first to seventh methods may be characterized as a production method (designated as "eighth method") in which the cis-1,3,3,3-tetrafluoropropene is brought into contact with the metal oxide at 10 to 80° C.

Any one of the first to eighth methods may be characterized as a production method (designated as "ninth method") in which the cis-1,3,3,3-tetrafluoropropene is in the form of a mixture containing at least cis-1,3,3,3-tetrafluoropropene.

DETAILED DESCRIPTION

The method of the present invention enables selective and efficient conversion of cis-1,3,3,3-tetrafluoropropene to trans-1,3,3,3-tetrafluoropropene as a technique for industrial production of trans-1,3,3,3-tetrafluoropropene.

The method of the present invention is thus suitable for industrial manufacturing of blowing agents for rigid polyurethane foams, solvents, detergents, refrigerants, hydraulic fluids, propellants, raw materials for fluoropolymers and the like because of the ease of production of the trans-1,3,3,3-tetrafluoropropene.

The production method of trans-1,3,3,3-tetrafluoropropene according to the present invention includes an isomerization reaction of cis-1,3,3,3-tetrafluoropropene by contact with either a metal oxide catalyst or a metal compound-supported catalyst.

The reaction can be conducted in either a gas phase or a liquid phase. Further, the reaction can be conducted by either a continuous process or a batch process. Any appropriate combination of the reaction phase and the reaction process can be selected. In practice, it is particularly preferable to conduct the reaction in a continuous gas phase system in view of the fact that reaction involves chemical materials of low boiling points. In the continuous gas phase system, the catalyst can be used in a fixed bed, a fluidized bed or a movable bed. Among others, the fixed bed is preferred for ease of use.

The following explanations are specifically given to the gas phase reaction system. It is however obvious, in the case of the liquid phase reaction system, that a person skilled in the art will be able to make appropriate modifications for optimization of the reaction system based on any technical common sense.

There is no particular restriction on the preparation process of the cis-1,3,3,3-tetrafluoropropene used in the present invention. The cis-1,3,3,3-tetrafluoropropene can be prepared by any known process. For example, it is feasible to prepare the 1,3,3,3-tetrafluoropropene by a fluorination reaction of 1-chloro-3,3,3-trifluoropropene with hydrogen fluoride in the presence of a Ti/C or Cr/C catalyst (Patent Document 1). It is also feasible to prepare the 1,3,3,3-tetrafluoropropene by a dehydrofluorination reaction of 1,1,1,3,3-pentafluoropropane in a gas phase by contact with a carbon or a metal-supported carbon in an elevated-temperature reaction range (Patent Document 2).

In each of these processes, the 1,3,3,3-tetrafluoropropene is prepared as a mixture of cis and trans isomers. Such a mixture can be used as it is as the raw material in the production method of the present invention, irrespective of the ratio of the cis and trans isomers. As a matter of course, only the cis isomer of 1,3,3,3-tetrafluoropropene can alternatively be used as the raw material. Further, the isomerization reaction product of the method of the present invention may consist substantially of trans-1,3,3,3-tetrafluoropropene or may contain an increased amount of trans-1,3,3,3-tetrafluoropropene.

In the case of preparing the cis- and trans-isomer mixture of the 1,3,3,3-tetrafluoropropene by the fluorination reaction of 1-chloro-3,3,3-trifluoropropene with hydrogen fluoride in the presence of the Ti/C or Cr/C catalyst as mentioned above, the resulting reaction mixture contains hydrogen chloride as a by-product and any other side reaction product(s). In the other preparation process, hydrogen fluoride and/or the like may be entrained in the reaction product. In the method of the present invention, the cis-1,3,3,3-tetrafluoropropene can be subjected to the isomerization reaction without purification thereof for production of the trans-1,3,3,3-tetrafluoropropene.

The method of the present invention can be performed by using a reactor made of a material substantially inert to hydrogen fluoride, and introducing the cis-1,3,3,3-tetrafluoropropene to a reaction area of the reactor in which the catalyst is charged and placed under controlled temperature conditions. In general, the reactor is formed into a cylindrical shape and made of stainless steel, Hastelloy™, Monel™, platinum, carbon material, fluoropolymer etc. or lined materials thereof.

There is no particular restriction on the catalyst used in the present invention as long as the catalyst is capable of converting the cis-1,3,3,3-tetrafluoropropene to the trans-1,3,3,3-tetrafluoropropene by contact of the cis-1,3,3,3-tetrafluoropropene with the catalyst. The metal oxide and the metal oxide-supported catalyst exemplify such a catalyst.

The metal oxide used in the present invention contains at least one kind of metal selected from the group consisting of aluminum, chromium, zirconium, titanium and magnesium. The oxides of these metals can be used solely. The metal oxide can alternatively be a composite oxide of two or more kinds of these metals. In the present specification, the term "metal oxide" may include a "fluorinated metal oxide".

The metal oxide used as the catalyst in the present invention can be prepared by any known catalyst preparation process. One example of the catalyst preparation process is to neutralize a water-soluble salt of the metal oxide with ammonia, dry the resulting hydroxide sol precipitates, pulverize the dried clusters into powder and cast molds, and then, bake the mold. At this time, a compound of at least one metal, other than the main metal component, selected from the group consisting of aluminum, chromium, titanium, manganese, iron, nickel, cobalt, magnesium, zirconium and antimony may be used in combination for preparation of the composite oxide. Preferred examples of the composite oxide are an alumina-chromium composite oxide, an alumina-zirconia composite oxide, an alumina-titania composite oxide and an alumina-magnesia composite oxide. These composite oxides preferably have an aluminum content of 50 atomic % or more, more preferably 80 atomic % or more. If the aluminum content of the composite oxide is less than 50 atomic %, the reaction rate of the isomerization reaction becomes unfavorably lowered.

The metal oxide is commercially available in various forms as catalysts or drying agents. Any of such commercially available metal oxides can be selected for use. Although the metal oxide can be in powder form, grains of the metal oxide are in common use. The shape and size of the metal oxide grains are not particularly restricted and can be determined from common knowledge on the basis of the size of the reactor. The metal oxide grains commonly used are those formed into a spherical shape, a rodlike shape or a tablet shape with an average diameter or length of about 1 to 10 mm for ease of handling. There are one or more crystalline forms of the metal oxide. For example, the crystalline forms of the alumina include α-alumina and γ-alumina; and the crystalline forms of the titania includes anatase and rutile. The metal oxide can have any crystalline form. Among the alumina crystalline forms, γ-alumina is preferred because of its large surface area.

In the method of the present invention, the metal oxide is generally used in the form of a fluorinated metal oxide. In the case of using the metal oxide in non-fluorinated form, the 1,3,3,3-tetrafluoropropene acts as a fluorination agent to convert the non fluorinated metal oxide to the fluorinated metal oxide over time so that the reaction tends to become unstable. It is thus preferable to prepare the metal oxide in fluorinated form, or treat the metal oxide with a fluorination agent in advance of the reaction.

As the metal oxide, there can preferably be used a fluorinated metal oxide having a part of oxygen atoms substituted with fluorine atoms or a fluoride having all of oxygen atoms substituted with fluorine atoms. The ratio of substitution of the oxygen atoms by the fluorine atoms is not particularly restricted and can be varied in a wide range.

The fluorinated metal oxide is prepared by contact with a fluorination agent such as hydrogen fluoride, fluorohydrocarbon or chlorofluorohydrocarbon. In general, the fluorination is preferably carried out in a step-by-step manner. As the fluorination with hydrogen fluoride is accompanied by large heat generation, it is desirable to use a diluted aqueous hydrogen fluoride solution or hydrogen fluoride gas at a relatively low temperature in an initial stage of the fluorination and then gradually increase the hydrogen fluoride concentration and/or fluorination temperature. It is further preferable, in a final stage of the fluorination, to control the temperature to be higher than or equal to the reaction temperature of the isomerization reaction. In addition to this, it is preferable to control the fluorination temperature to 200° C. or higher, more preferably 400° C. or higher, still more preferably 500° C. or higher, in the fluorination with hydrogen fluoride, so as to avoid aging variations during the reaction. The upper limit of the fluorination temperature is not particularly restricted. In view of the thermal resistance of fluorination treatment equipment, the fluorination is difficult to conduct at a temperature of higher than 900° C. It is preferable to conduct the fluorination at a temperature of 600° C. or lower for practical application.

The metal oxide is preferably treated, before use, with the fluorination agent such as hydrogen fluoride, fluorohydrocarbon or chlorofluorohydrocarbon as mentioned above at temperatures higher than the predetermined reaction temperature so as to avoid a composition variation in the catalyst during the reaction.

The metal-supported catalyst used in the present invention has, as a support, a carbon or a metal oxide or fluorinated metal oxide of the same kind as mentioned above.

In general, an activated carbon is used as a carbon support. Examples of the activated carbon are: plant-based activated carbons using wood, sawdust, charcoal, coconut shell charcoal, palm kernel charcoal, black ash etc. as raw materials; coal-based activated carbons using peat coal, lignite, brown coal, bituminous coal, anthracite coal etc. as raw materials; petroleum-based activated carbons using asphalt, acid sludge, oil carbon etc. as raw materials; and synthetic resin-based activated carbons.

Various kinds of the activated carbon are commercially available. Any such a commercially available activated carbon can be selected for use. Examples of the commercially available activated carbon are bituminous coal activated carbons (such as "Calgon Granular Activated Carbon CAL" manufactured by Toyo Calgon Co., Ltd.) and coconut shell activated carbons (such as "Granular SHIRASAGI G series" manufactured by Japan Enviro Chemicals Ltd.) The activated carbon is not however limited to those of the above kinds and manufacturers.

The activated carbon is generally used in the form of particles such as crushed activated carbon, granular activated carbon, granulated activated carbon or spherical activated carbon. The shape and size of the activated carbon particles are not particularly restricted and can be determined from common knowledge on the basis of the size of the reactor. The activated carbon particles commonly used are those formed into a spherical shape with an average diameter of about 1 to 10 mm for ease of handling.

Preferred examples of the metal of the supported metal compound are aluminum, chromium, titanium, manganese, iron, nickel, cobalt, magnesium, zirconium and antimony. In particular, aluminum, chromium, titanium, zirconium and antimony are preferred. These metals are used in the form of oxides, fluorides, chlorides, chlorofluorides, oxyfluorides, oxychlorides, oxychlorofluorides etc. Two or more kinds of metal compounds may be used in combination.

There is no particular restriction on the metal supporting process. The metal supporting process can be performed by impregnating, or spraying, the support with a solution containing a soluble compound of one kind or two or more kinds of metals selected from the group consisting of aluminum, chromium, titanium, manganese, iron, nickel, cobalt, magnesium, zirconium and antimony, and then, dry the metal compound onto the carrier.

The metal content of the catalyst (expressed as the ratio of the mass of the supported metal to the total mass of the catalyst, the same applies to the following) is generally 0.1 to 80 mass %, preferably 1 to 50 mass %. There arise unfavorable effects such that; the activity of the catalyst is low if the metal content is less than 0.1 mass %; and it is difficult to support the metal compound stably on the carrier if the metal content exceeds 80 mass %.

As the soluble supported metal compound, there can be used a nitrate, a chloride and an oxide of the corresponding metal soluble in e.g. water, ethanol or acetone solvent. In the case of using antimony pentachloride that is liquid at room temperature, it is not necessary to use the solvent.

Specific examples of such a compound are chromium nitrate, chromium trichloride, chromium trioxide, potassium dichromate, titanium trichloride, manganese nitrate, manganese chloride, manganese dioxide, ferric chloride, nickel nitrate, nickel chloride, cobalt nitrate, cobalt chloride, antimony pentachloride, magnesium chloride, magnesium nitrate, zirconium chloride and zirconium nitrate.

It is preferable to treat the metal compound-supported catalyst, before use, with a fluorination agent such as hydrogen fluoride, fluorohydrocarbon or chlorofluorohydrocarbon at temperatures higher than the predetermined reaction temperature in the same manner as the case of the metal oxide catalyst, so as to avoid a composition variation in the catalyst during the isomerization reaction.

In the case of using either the metal oxide or supported catalyst in the present invention, it is effective to flow oxygen, chloride, fluorohydrocarbon, chlorofluorohydrocarbon, chlorohydrocarbon or the like into the reactor during the reaction for extended catalyst life and improved reaction yield and rate.

There is no particular restriction on the temperature of the isomerization reaction in the present invention. The isomerization reaction temperature is generally −10 to 400° C., preferably 0 to 300° C., more preferably 10 to 250° C., still more preferably 10 to 80° C. If the reaction temperature is lower than −10° C., there arise unfavorable effects such as a need to provide special cooling equipment in the reactor and a disadvantage in terms of energy efficiency. On the other hand, the reaction rate is not specifically improved even if the reaction temperature exceeds 400° C. In such a high temperature range, there arises unfavorable effects such as a deterioration in the selectivity of the trans-1,3,3,3-tetrafluoropropene due to a decomposition product. It is particularly preferable in the gas phase reaction system to control the reaction temperature range to −10 to 400° C., preferably 0 to 300° C., more preferably 10 to 250° C., still more preferably 10 to 80° C.

In the method of the present invention, the cis-1,3,3,3-tetrafluoropropene may be supplied, to the reaction area, together with a gas irrelevant to the reaction e.g. nitrogen, helium, argon etc. The amount of this gas is 100 moles or less, preferably 10 moles or less, per 1 mole of the cis-1,3,3,3-tetrafluoropropene or the mixture thereof used as the raw material. In general, it is preferable not to use such an additional gas.

There is also no particular restriction on the pressure in the method of the present invention. Although the reaction in the gas phase reaction system does not specifically require pressure control by pressurization or reduction, it is preferable in the gas phase reaction system to conduct the reaction under a pressure of 0.01 to 1 MPa (absolute pressure) in terms of equipment. The pressure is preferably controlled to such a level that the organic raw material does not become liquefied in the reaction system. It is preferable in the liquid phase reaction system to conduct the reaction under pressurized conditions because of low boiling points of the cis- and trans-1,3,3,3-tetrafluoropropene raw materials.

In the method of the present embodiment, the contact time is generally 0.1 to 500 seconds, preferably 30 to 300 seconds, under standard conditions. The reaction rate is undesirably lowed if the contact time is too short. If the contact time is too long, there occurs an undesirable side reaction.

The isomerization reaction product of the method of the present invention, discharged out of the reactor, can be purified to a final product by any known process.

There is no particular restriction on the purification process. For example, the trans-1,3,3,3-tetrafluoropropene can be obtained by first washing the product with water and/or an alkaline solution and thereby removing any acid substance such as hydrogen fluoride, drying the product, and then, removing the cis-1,3,3,3-tetrafluoropropene and other organic impurity by distillation. The separated cis-1,3,3,3-tetrafluoropropene can be reused as the raw material of the isomerization reaction.

EXAMPLES

The present invention will be described in more detail below by way of the following examples. It should be noted that these examples are illustrative only and are not intended to limit the present invention thereto. Herein, the term "%" of a composition analysis value represents "area%" of an organic component in a reaction mixture as measured by gas chromatography (using a flame ionization detector FID, unless otherwise specified).

Preparation Example 1

A jacketed reactor tube was charged with 160 g of granular γ-alumina (available under the trade name of KHS-46 from Sumika Alchem Co., Ltd.) and heated to 150° C. Then, hydrogen fluoride was introduced into the reactor tube at a flow rate of 15 g/hr continuously until a hot spot reached an outlet of the reactor tube.

Examples 1 and 2

A gas-phase reactor having a cylindrical reactor tube (material: SUS316L, diameter: 2.5 cm, length: 40 cm) with an external heater was charged with 50 ml of the catalyst prepared in Preparation Example 1. The reactor tube was heated to 100° C. while flowing a nitrogen gas into the reactor tube at a flow rate of about 20 ml/min. Hydrogen fluoride was then introduced into the reactor tube at a flow rate of about 0.1 to 0.2 g/min over 1 hour. The temperature of the reactor tube was raised to 200° C. The hydrogen fluoride was introduced into the reactor tube at a flow rate of about 0.1 to 0.2 g/min over 1 hour. The hydrogen fluoride was further introduced into the reactor tube at a flow rate of about 0.3 to 0.4 g/min while the temperature of the reactor tube was raised to 380° C. in 30 minutes. In this state, the catalyst treatment was continued for 2 hours.

Next, the temperature of the reactor tube was changed to 325° C. The flow rate of the nitrogen gas was reduced to 10 ml/min. A mixture of cis- and trans-1,3,3,3-tetrafluoropropenes (cis isomer: 67.71%, trans isomer: 1.46%, the balance being 1,1,1,3,3-pentafluoropropene, the same applies to the following), which had previously been vaporized, was supplied as an organic raw material into the reactor tube at a flow rate of 0.05 g/min (contact time: 71 seconds).

The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 1 (Example 1).

Subsequently, the temperature of the reactor tube was changed to 50° C. (Example 2). After the reaction was stabilized, the gas from the reactor was blown into water to remove an acid gas component. The thus-obtained reaction gas product was analyzed by gas chromatography. The analysis results are indicated in TABLE 1 (Example 2).

Preparation Example 2

A jacketed reactor tube was charged with 160 g of granular γ-alumina (available under the trade name of KHS-46 from Sumika Alchem Co., Ltd.) and heated to 150° C. Then, hydrogen fluoride was introduced into the reactor tube at a flow rate of 15 g/hr continuously until a hot spot reached an outlet of the reactor tube.

Example 3

A gas-phase reactor having a cylindrical reactor tube (material: SUS316L, diameter: 2.5 cm, length: 40 cm) with an external heater was charged with 50 ml of the catalyst prepared in Preparation Example 2. The reactor tube was heated to 100° C. while flowing a nitrogen gas into the reactor tube at a flow rate of about 20 ml/min. Hydrogen fluoride was then introduced into the reactor tube at a flow rate of about 0.1 to 0.2 g/min over 1 hour. The temperature of the reactor tube was raised to 200° C. The hydrogen fluoride was further introduced into the reactor tube at a flow rate of about 0.1 to 0.2 g/min over 1 hour.

The temperature of the reactor tube was changed to 50° C. The flow rate of the nitrogen gas was reduced to 10 ml/min. A mixture of cis- and trans-1,3,3,3-tetrafluoropropenes (cis isomer: 67.71%, trans isomer: 1.46%), which had previously been vaporized, was supplied as an organic raw material into the reactor tube at a flow rate of 0.05 g/min (contact time: 131 seconds). After a lapse of 2 hours from the initiation of the reaction, the gas from the reactor was blown into water to remove an acid gas component. The thus-obtained reaction gas product was analyzed by gas chromatography. The analysis results are indicated in TABLE 1.

Preparation Example 3

A jacketed reactor tube was charged with 160 g of granular γ-alumina (available under the trade name of KHS-46 from Sumika Alchem Co., Ltd.) and heated to 150° C. Hydrogen fluoride was then introduced into the reactor tube at a flow rate of 15 g/hr continuously until a hot spot reached an outlet of the reactor tube.

Example 4

A gas-phase reactor having a cylindrical reactor tube (material: SUS316L, diameter: 2.5 cm, length: 40 cm) with an external heater was charged with 50 ml of the catalyst prepared in Preparation Example 3. The reactor tube was heated to 100° C. while flowing a nitrogen gas into the reactor tube at a flow rate of about 20 ml/min. Hydrogen fluoride was then introduced into the reactor tube at a flow rate of about 0.1 to 0.2 g/min over 1 hour. The temperature of the reactor tube was raised to 200° C. The hydrogen fluoride was introduced into the reactor tube at a flow rate of about 0.1 to 0.2 g/min over 1 hour. The hydrogen fluoride was further introduced into the reactor tube at a flow rate of about 0.3 to 0.4 g/min while raising the temperature of the reactor tube to 500° C. in 1 hour. In this state, the catalyst treatment was continued for 2 hours.

The reactor tube was cooled down to 50° C. While maintaining the temperature of the reactor tube, the flow rate of the nitrogen gas was reduced to 10 ml/min. A mixture of cis- and trans-1,3,3,3-tetrafluoropropenes (cis isomer: 67.71%, trans isomer: 1.46%), which had previously been vaporized, was supplied as an organic raw material into the reactor tube at a flow rate of 0.05 g/min (contact time: 131 seconds).

The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 1.

Preparation Example 4

A 20 mass % aqueous $CrCl_3$ solution was prepared by diluting a commercially available reagent of 40 mass % $CrCl_3$ aqueous solution. Then, 100 g of granular activated carbon of 4 to 6 mm in diameter, 1200 $m^2/g$ in surface area, 18 angstroms in pore size (available under the trade name of Granular SHIRASAGI GX from Japan Enviro Chemicals Ltd.) was kept immersed in the prepared 20 mass % $CrCl_3$ aqueous solution for one day. The resulting activated carbon was taken out by filtration and dried at 100° C. in a hot-air circulation drier for one day.

The thus-obtained chromium-supported activated carbon was charged into a cylindrical reactor tube formed of SUS316L with a diameter of 2.5 cm and a length of 40 cm and equipped with an external heater. The reactor tube was heated to 300° C. while flowing a nitrogen gas into the reactor tube. At the time there occurred no water discharge from the reactor tube, the nitrogen gas was accompanied with hydrogen fluoride. The concentration of the hydrogen fluoride was gradually increased. Further, the temperature of the reactor was raised to 350° C. In this state, the catalyst treatment was continued for 1 hour.

Example 5

A gas-phase reactor having a cylindrical reactor tube (material: SUS316L, diameter: 2.5 cm, length: 40 cm) with an external heater was charged with 50 ml of the catalyst prepared in Preparation Example 4. The reactor tube was heated to 100° C. after flowing a nitrogen gas into the reactor tube at a flow rate of about 20 ml/min. Hydrogen fluoride was then introduced into the reactor tube at a flow rate of about 0.1 to 0.2 g/min over 1 hour. The temperature of the reactor tube was raised to 200° C. The hydrogen fluoride was introduced into the reactor tube at a flow rate of about 0.1 to 0.2 g/min over 1 hour. The hydrogen fluoride was further introduced into the reactor tube over 1 hour in the same manner as above while raising the temperature of the reactor tube to 350° C.

The temperature of the reactor tube was changed to 325° C. The flow rate of the nitrogen gas was reduced to 15 ml/min. A mixture of cis- and trans-1,3,3,3-tetrafluoropropenes (cis isomer: 67.71%, trans isomer: 1.46%), which had previously been vaporized, was supplied as an organic raw material into the reactor tube at a flow rate of 0.13 g/min (contact time: 35 seconds). The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 1.

Comparative Example 1

A gas-phase reactor having a cylindrical reactor tube (material: SUS316L, diameter: 2.5 cm, length: 40 cm) with an external heater was charged with 50 ml of granular activated carbon of 4 to 6 mm in diameter, 1200 $m^2/g$ in surface area, 18 angstroms in pore size (available under the trade name of Granular SHIRASAGI GX from Japan Enviro Chemicals Ltd.) as a catalyst. The reactor tube was heated to 100° C. while flowing a nitrogen gas into the reactor tube at a flow rate of about 20 ml/min. Hydrogen fluoride was then introduced into the reactor tube at a flow rate of about 0.1 to 0.2 g/min over 1 hour. The temperature of the reactor tube was raised to 200° C. The hydrogen fluoride was introduced into the reactor tube at a flow rate of about 0.1 to 0.2 g/min over 1 hour. The hydrogen fluoride was further introduced into the reactor tube in the same manner as above while raising the temperature of the reactor tube to 350° C.

The temperature of the reactor tube was changed to 325° C. The flow rate of the nitrogen gas was reduced to 15 ml/min. A mixture of cis- and trans-1,3,3,3-tetrafluoropropenes (cis isomer: 67.71%, trans isomer: 1.46%), which had previously been vaporized, was supplied as an organic raw material into the reactor tube at a flow rate of 0.13 g/min (contact time: 35 seconds). The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 1.

TABLE 1

| Example | Catalyst Kind | Treatment temperature | Reaction temperature ° C. | Contact time sec |
|---|---|---|---|---|
| Raw material | | | | |
| 1 | alumina | 380° C. | 325° C. | 71 |
| 2 | alumina | 380° C. | 50° C. | 131 |
| 3 | alumina | 200° C. | 50° C. | 131 |
| 4 | alumina | 500° C. | 50° C. | 131 |
| 5 | Cr/C | 350° C. | 325° C. | 35 |
| Comparative Example 1 | activated carbon | 350° C. | 325° C. | 35 |

| Example | Composition (area %) | | | Isomer ratio |
| | cis-1234 | trans-1234 | 245fa | cis/trans |
|---|---|---|---|---|
| Raw material | 67.71 | 1.46 | 30.76 | 98/2 |
| 1 | 17.23 | 76.40 | 5.84 | 18/82 |

TABLE 1-continued

| 2 | 4.29 | 61.87 | 33.78 | 6/94 |
| 3 | 4.25 | 62.09 | 33.59 | 6/94 |
| 4 | 4.24 | 62.10 | 33.56 | 6/94 |
| 5 | 18.00 | 74.76 | 7.24 | 19/81 |
| Comparative Example 1 | 61.45 | 7.68 | 30.70 | 89/11 | cis-1234; cis-1,3,3,3-tetrafluropropene
trans-1234; trans-1,3,3,3-tetrafluoropropene
245fa; 1,1,1,3,3-pentafluoropropene

Examples 6 to 10

A catalyst was prepared and pretreated in the same manner as in Preparation Example 1 and Example 1.

The temperature of the reactor tube was changed to 150° C. The flow rate of the nitrogen gas was reduced to 10 ml/min. A mixture of cis- and trans-1,3,3,3-tetrafluoropropenes (cis isomer: 63.0%, trans isomer: 1.7%), which had previously been vaporized, was supplied as an organic raw material into the reactor tube at a flow rate of 0.05 g/min (contact time: 63 seconds).

The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 2 (Example 6).

Subsequently, the temperature of the reactor tube was changed to 100° C. (Example 7), 80° C. (Example 8), 50° C. (Example 9), and then, to 20° C. (Example 10). After the reaction was stabilized, the gas from the reactor was blown into water to remove an acid gas component. The thus-obtained reaction gas product was analyzed by gas chromatography. The analysis results are indicated in TABLE 2 (Examples 6, 7, 8, 9 and 10).

TABLE 2

| Example | Catalyst | | Reaction temperature ° C. | Contact time sec |
|---|---|---|---|---|
| | Kind | Treatment temperature | | |
| Raw material | | | | |
| 6 | alumina | 380° C. | 150° C. | 63 |
| 7 | alumina | 380° C. | 100° C. | 72 |
| 8 | alumina | 380° C. | 80° C. | 76 |
| 9 | alumina | 380° C. | 50° C. | 83 |
| 10 | alumina | 380° C. | 20° C. | 91 |

| Example | Composition (area %) | | | Isomer ratio |
|---|---|---|---|---|
| | cis-1234 | trans-1234 | 245fa | cis/trans |
| Raw material | 63.0 | 1.7 | 35.2 | 97/3 |
| 6 | 6.3 | 59.3 | 34.1 | 10/90 |
| 7 | 5.4 | 60.7 | 33.9 | 8/92 |
| 8 | 4.6 | 61.6 | 33.7 | 7/93 |
| 9 | 4.1 | 62.1 | 33.7 | 6/94 |
| 10 | 2.8 | 63.7 | 33.4 | 4/96 | cis-1234; cis-1,3,3,3-tetrafluropropene
trans-1234; trans-1,3,3,3-tetrafluoropropene
245fa; 1,1,1,3,3-pentafluoropropene

Examples 11 and 12

A catalyst was prepared and pretreated in the same manner as in Preparation Example 1 and Example 1.

The temperature of the reactor tube was changed to 325° C. The flow rate of the nitrogen gas was reduced to 10 ml/min. A mixture of cis- and trans-1,3,3,3-tetrafluoropropenes (cis isomer: 99.8%), which had previously been vaporized, was supplied as an organic raw material into the reactor tube at a flow rate of 0.05 g/min (contact time: 43 seconds).

The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 3 (Example 11).

Subsequently, the temperature of the reactor tube was changed to 50° C. After the reaction was stabilized, the gas from the reactor was blown into water to remove an acid gas component. The thus-obtained reaction gas product was analyzed by gas chromatography. The analysis results are indicated in TABLE 3 (Example 12).

Examples 13 and 14

A catalyst was prepared and pretreated in the same manner as in Preparation Example 1 and Example 1.

The temperature of the reactor tube was changed to room temperature (26° C.). The flow rate of the nitrogen gas was reduced to 10 ml/min. A mixture of cis- and trans-1,3,3,3-tetrafluoropropenes (cis isomer: 77.3%, trans isomer: 0.1%), which had previously been vaporized, was supplied as an organic raw material into the reactor tube at a flow rate of 0.27 g/min (contact time: 44 seconds).

The reaction was stabilized after a lapse of 2 hours from the initiation of the reaction. The gas from the reactor was blown into water to remove an acid gas component. The thus-obtained reaction gas product was analyzed by gas chromatography. The analysis results are indicated in TABLE 3 (Example 13).

Subsequently, the supply rate of the organic raw material was changed to 0.12 g/min (contact time: 90 seconds). After the reaction was stabilized, the gas from the reactor was blown into water to remove an acid gas component. The thus-obtained reaction gas product was analyzed by gas chromatography. The analysis results are indicated in TABLE 3 (Example 14).

TABLE 3

| Example | Catalyst | | Reaction temperature ° C. | Contact time sec |
|---|---|---|---|---|
| | Kind | Treatment temperature | | |
| Raw material | | | | |
| 11 | alumina | 380° C. | 325° C. | 43 |
| 12 | alumina | 380° C. | 50° C. | 80 |
| Raw material | | | | |
| 13 | alumina | 380° C. | 26° C. | 44 |
| 14 | alumina | 380° C. | 26° C. | 83 |

| Example | Composition (area %) | | | Isomer ratio |
|---|---|---|---|---|
| | cis-1234 | trans-1234 | 245fa | cis/trans |
| Raw material | 99.8 | — | — | 100/0 |
| 11 | 18.1 | 81.0 | — | 18/82 |
| 12 | 6.1 | 93.3 | — | 6/94 |
| Raw material | 77.3 | 0.1 | 21.6 | 100/0 |
| 13 | 3.9 | 74.4 | 21.3 | 5/95 |
| 14 | 3.8 | 74.5 | 21.3 | 5/95 | cis-1234; cis-1,3,3,3-tetrafluropropene
trans-1234; trans-1,3,3,3-tetrafluoropropene
245fa; 1,1,1,3,3-pentafluoropropene

The invention claimed is:

1. A method of producing trans-1,3,3,3-tetrafluoropropene, comprising: bringing cis-1,3,3,3-tetrafluoropropene into contact with a catalyst,
wherein the catalyst comprises a metal oxide that contains aluminum and at least one other metal selected from the group consisting of chromium, titanium, manganese, iron, nickel, cobalt, magnesium, zirconium and antimony, and wherein the metal oxide comprises at least 50 atomic % of aluminum in terms of metal atoms.

2. The method according to claim 1, wherein the metal oxide is a fluorinated metal oxide having a part or all of oxygen atoms substituted with fluorine atoms.

3. A method of producing trans-1,3,3,3-tetrafluoropropene, comprising: bringing cis-1,3,3,3-tetrafluoropropene into contact with a catalyst,
wherein the catalyst is a supported catalyst comprising at least one of chromium nitrate, chromium trichloride, chromium trioxide, potassium dichromate, titanium trichloride, manganese nitrate, manganese chloride, manganese dioxide, ferric chloride, nickel nitrate, nickel chloride, cobalt nitrate, cobalt chloride, antimony pentachloride, magnesium chloride, magnesium nitrate, zirconium chloride and zirconium nitrate, supported on carbon.

4. The method according to claim 1, wherein the cis-1,3,3,3-tetrafluoropropene is brought into contact, in a gas phase, with the metal oxide.

5. The method according to claim 1, wherein the cis-1,3,3,3-tetrafluoropropene is brought into contact with the metal oxide at −10 to 400° C.

6. The method according to claim 1, wherein the cis-1,3,3,3-tetrafluoropropene is brought into contact with the metal oxide at 10 to 80° C.

7. The method according to claim 1, wherein the cis-1,3,3,3-tetrafluoropropene is in the form of a mixture.

8. The method according to claim 3, wherein the cis-1,3,3,3-tetrafluoropropene is brought into contact, in a gas phase, with the catalyst.

9. The method according to claim 3, wherein the cis-1,3,3,3-tetrafluoropropene is brought into contact with the catalyst at −10 to 400° C.

10. The method according to claim 3, wherein the cis-1,3,3,3-tetrafluoropropene is brought into contact with the catalyst at 10 to 80° C.

11. The method according to claim 3, wherein the cis-1,3,3,3-tetrafluoropropene is in the form of a mixture.

* * * * *